United States Patent [19]

Buck et al.

[11] Patent Number: 5,733,323
[45] Date of Patent: Mar. 31, 1998

[54] ELECTRICALLY CONDUCTIVE UNIPOLAR VASCULAR SHEATH

[75] Inventors: Jerrick Buck, Miami; Daniel S. Goldman, Atlantic Beach; Donald J. Larnard, Boca Raton, all of Fla.

[73] Assignee: Cordis Corporation, Miami Lakes, Fla.

[21] Appl. No.: 558,641

[22] Filed: Nov. 13, 1995

[51] Int. Cl.⁶ .................................................... A61N 1/05
[52] U.S. Cl. ........................................ 607/122; 128/642
[58] Field of Search ................... 128/642; 607/98–101, 607/116, 119, 122; 606/32, 40, 41

[56] References Cited

U.S. PATENT DOCUMENTS

| 452,220 | 5/1891 | Gunning ............................ 607/116 |
|---|---|---|
| 4,440,108 | 4/1984 | Little et al. . |
| 4,526,637 | 7/1985 | Long . |
| 4,611,604 | 9/1986 | Botvidsson et al. ................ 607/122 |
| 4,693,760 | 9/1987 | Sioshansi . |
| 4,743,493 | 5/1988 | Siochansi et al. . |
| 4,855,026 | 8/1989 | Sioshansi . |
| 4,968,006 | 11/1990 | Oliver . |
| 5,098,483 | 3/1992 | Little et al. . |
| 5,104,690 | 4/1992 | Greenwald . |
| 5,118,400 | 6/1992 | Wollam . |
| 5,123,924 | 6/1992 | Sioshansi et al. . |
| 5,133,757 | 7/1992 | Sioshansi et al. . |
| 5,409,008 | 4/1995 | Svenson et al. ..................... 128/642 |
| 5,429,130 | 7/1995 | Goldman . |
| 5,462,545 | 10/1995 | Wang et al. ..................... 607/116 X |
| 5,476,496 | 12/1995 | Strandberg et al. ................ 607/122 |

OTHER PUBLICATIONS

Biomaterials Surface Engineering Services "Surfaces Engineered for Superior Performance", Spire Corporation, (undated, received 1993).

*Primary Examiner*—Jeffrey R. Jastrzab
*Attorney, Agent, or Firm*—Lockwood, Alex, Fitz-Gibbon & Cummings

[57] ABSTRACT

An electrically conductive sheath introducer is provided which functions as a unipolar electrode as well as a percutaneous vascular sheath introducer for a catheter. Typically, the catheter will include an electrode at its distal portion, and a circuit will be developed which includes the electrode of the catheter and the electrically conductive sheath introducer. Various electrical procedures are thus possible, including recording and energy delivery. The sheath introducer is rendered electrically conductive by ion process deposition treatment of the polymeric material sheath with a metallic material or materials. The resulting electrically conductive sheath introducer exhibits an incredibly low resistivity and resistance.

29 Claims, 2 Drawing Sheets

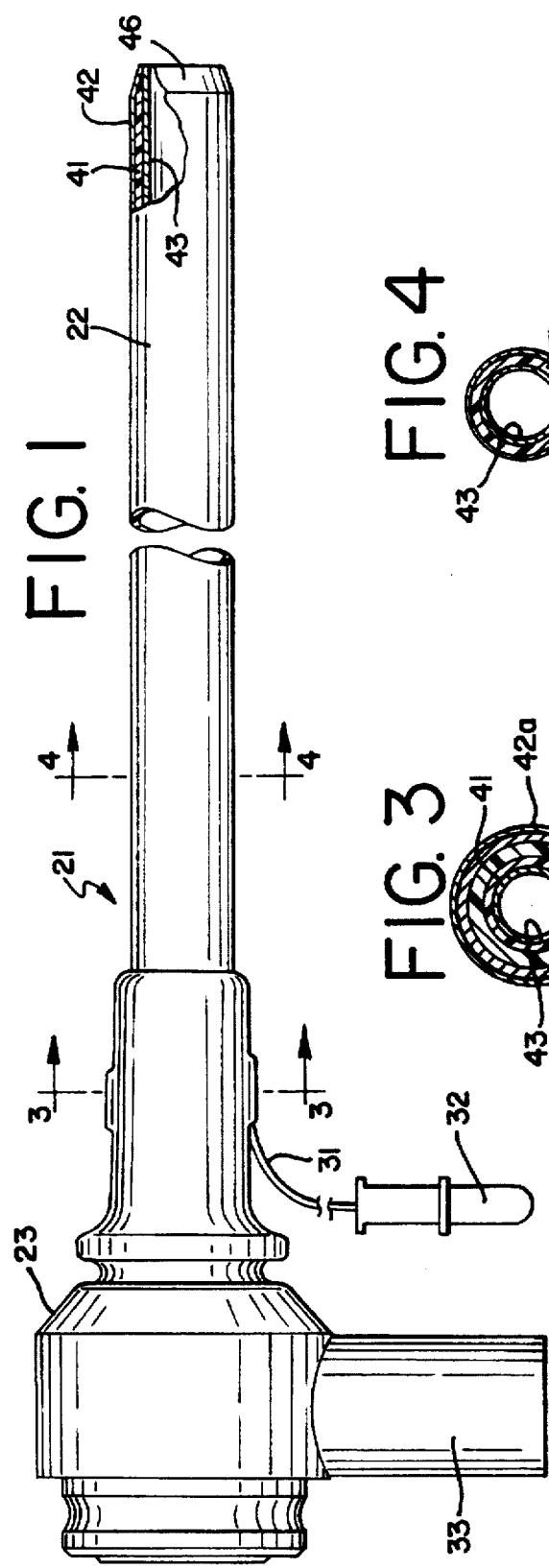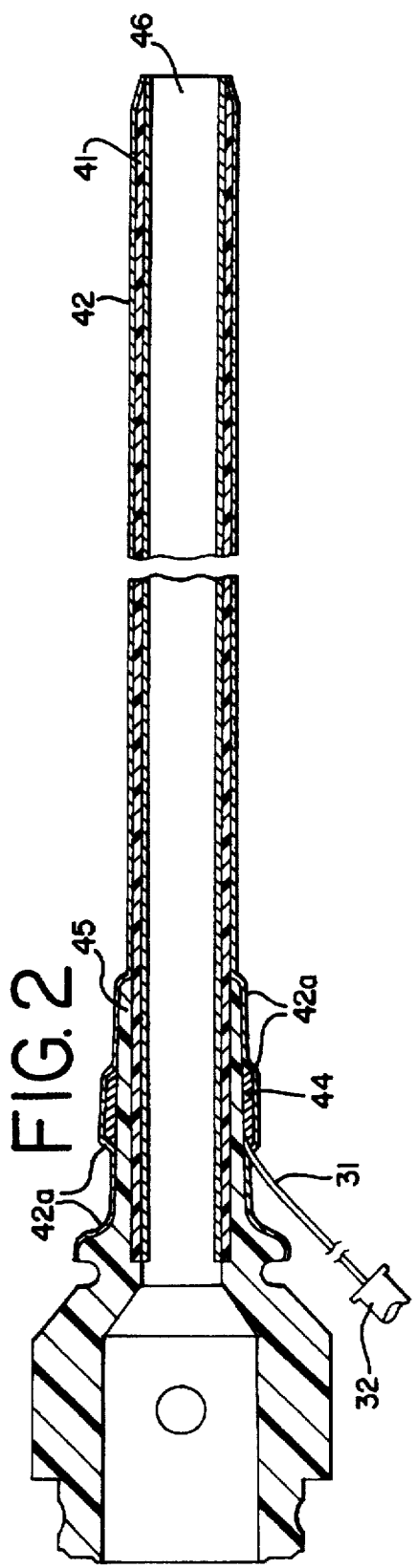

ELECTRICALLY CONDUCTIVE UNIPOLAR VASCULAR SHEATH

BACKGROUND AND SUMMARY OF THE INVENTION

The present invention generally relates to an electrically conductive percutaneous unipolar vascular sheath introducer having especially advantageous electrical properties. More particularly, the unipolar vascular sheath includes a conductive cannula shaft made of a polymeric material having an outer surface which is an adherent thin metallic material film that is of very low resistivity and that is chemically and/or mechanically bonded to the polymeric material of the cannula shaft in order to provide an indifferent electrode of low resistance.

Percutaneous vascular unipolar electrically conductive sheaths are generally described in Goldman U.S. Pat. No. 5,429,130, the disclosure thereof being incorporated by reference hereinto. In such devices, the sheath is inserted into the vascular system of a patient's body, the sheath serving as an indifferent electrode thereon and a conductor wire in electrical communication with the electrically conductive area on the outer coaxial surface of the sheath. This conductor is adapted to be connected to an external circuit. In addition, the sheath is adapted to receive a catheter having an electrode at its distal portion. When the external circuit is completed, with the inside being electrically insulated from the outside surface, it passes through the patient's body between the electrode of the catheter and the electrically conductive area of the sheath.

Devices such as these are intended for use in recording electrical signals Such as in carrying out mapping techniques. In addition, such devices can be for use in energy delivery to the patient's body, such as is accomplished in ablation procedures and related applications such as coagulation, electrical surgery and the like. For example, radio frequency (RF) current can be used. Devices of this type are suitable where an indifferent or ground connection is necessary.

The present invention is an improvement over devices such as those discussed hereinabove. The invention provides a sheath introducer having a cannula shaft that is both conductive and still flexible or malleable enough to be used in the same manner as, and to have substantially the same feel as, percutaneous vascular sheaths made principally of polymeric material and that are not conductive or that have a relatively small ring electrode or the like which does not substantially interfere with the flexibility or feel of the polymeric cannula shaft.

In summary, the present invention achieves certain objectives and provides advantageous properties by an electrically conductive percutaneous unipolar vascular sheath introducer which has a polymeric cannula shaft which is rendered conductive by having an elongated outer peripheral surface that is an electrically conductive surface which is an adherent, thin metallic material film that does not significantly alter the mechanical properties of the polymeric cannula shaft. This elongated conductive cannula shaft may function as an indifferent electrode which has an electrode surface area that is substantially coincident with the elongated outer peripheral surface of the cannula shaft. A conductor lead is in electrical communication with the electrically conductive surface of the cannula shaft. This arrangement allows the medical professional to insert an electrode-containing catheter into the body through the vascular sheath introducer. When, for example, the electrode of the catheter is in engagement with a portion of the heart, an electrical circuit can be provided between the catheter electrode and the external circuit, the circuit passing through the body and through the unipolar vascular sheath according to the invention.

It is accordingly a general object of the present invention to provide an improved electrically conductive sheath or cannula which is otherwise usable in the manner of a similarly sized sheath or cannula which is not electrically conductive.

Another object of the present invention is to provide an improved percutaneous unipolar vascular sheath introducer and method of providing and using same, which sheath introducer has a polymeric cannula shaft that is rendered electrically conductive over substantially its entire surface area.

Another object of the present invention is an improved electrically conductive percutaneous unipolar vascular sheath introducer and method of its preparation and use, which sheath introducer is polymeric and has been rendered electrically conductive by treatment with a conductive material on its surface.

Another object of the present invention is to provide an improved percutaneous unipolar vascular sheath that is electrically conductive over its surface and exhibits an extremely low resistance.

Another object of this invention is to provide an improved electrically conductive percutaneous unipolar vascular sheath which is primarily polymeric but which is treated with a very fine layer of treatment material that imparts its very low resistivity to substantially the entirety of the surface of the cannula shaft.

Another object of the present invention is to provide an improved sheath introducer which can act as an indifferent electrode for sensing or delivering current.

Another object of the present invention is to impart a metallic material coating to a sheath cannula which does not compromise or substantially impair the mechanical properties of the sheath cannula.

Another object of this invention is to provide a cannula having a metallic coating which actually enhances cannula mechanical tear and puncture resistance properties.

These and other objects, features and advantages of the present invention will be clearly understood through a consideration of the following detailed description.

BRIEF DESCRIPTION OF THE DRAWINGS

In the course of this description, reference will be made to the attached drawings, wherein:

FIG. 1 is an elevational view, partially broken away, of a preferred illustration of an electrically conductive percutaneous unipolar vascular sheath introducer in accordance with the present invention;

FIG. 2 is a transverse cross-sectional view through the sheath introducer embodiment illustrated in FIG. 1;

FIG. 3 is a cross-sectional view along the line 3—3 of FIG. 1;

FIG. 4 is a cross-sectional view along the line 4—4 of FIG. 1;

DESCRIPTION OF THE PARTICULAR EMBODIMENTS

Figure 5:
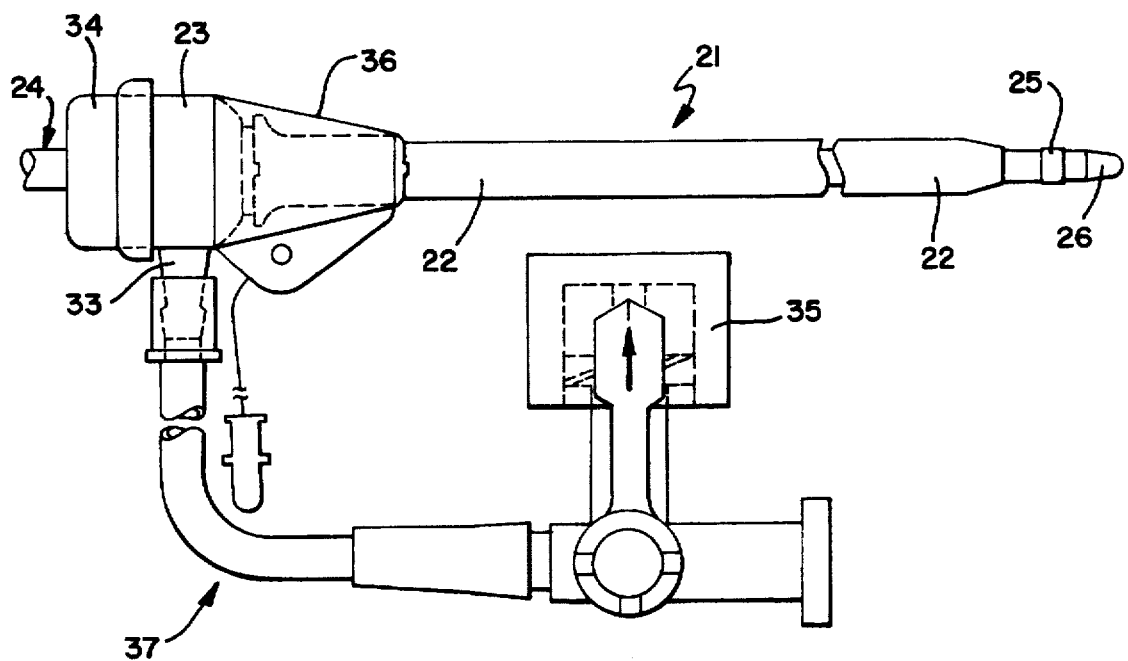
FIG. 5 is an elevational illustration of a sheath introducer in accordance with the present invention shown within an in-use application.

An illustration of a vascular sheath introducer that incorporates the present invention is generally designated as 21 in FIG. 1. Sheath introducer 21 includes an elongated conductive cannula shaft, generally designated as 22, and also includes a hub component 23 for facilitating attachment of the sheath introducer 21 to suitable treatment equipment and/or support devices, connectors and the like. Sheath introducer 21 is designed to receive a device such as a catheter, generally designated as 24 in FIG. 5 and in FIG. 6. As illustrated in FIG. 5, a typical catheter 24 can include one or more electrodes. Illustrated in this regard are a ring electrode 25 and a tip electrode 26. Electrodes of this type will be in engagement with the body tissue to be treated or diagnosed, such as an internal surface of a heart 27 of a patient 28. See FIG. 6 for an illustration of a typical procedure in this regard.

A conductor 31 is in electrical communication with the elongated conductive cannula shaft 22. It typically will include a pin jack 32 or other suitable connector so as to provide electrical communication with the equipment used for mapping, ablation and the like. In some applications a hollow tube or side arm sheath 33 is included for flushing and/or for optional fluid administration through the sheath introducer 21. FIG. 5 illustrates the following components useful in this regard. In addition to the cannula sheath introducer assembly 21, there is also provided a cap assembly 34 as shown in FIG. 5, as is a Luer cap 35. A collar structure 36 suitable for this use is also illustrated. These components are joined with a stopcock/tubing/collar assembly 37.

Figure 6:
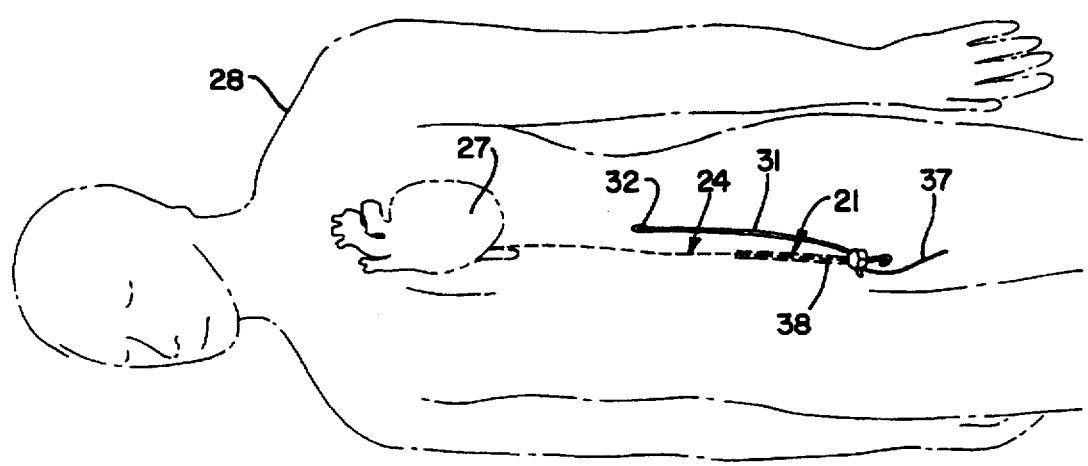
FIG. 6 is a schematic view illustrating a procedure practiced in accordance with the present method of use and illustrating an in-use environment of the electrically conductive unipolar sheath introducer in accordance with the present invention.

A typical use of the present invention is illustrated in FIG. 6. A puncture 38 is made in the patient, for example in the groin area as illustrated. The sheath introducer 21 is inserted inside the incision and into the blood vessel or the like. It will be appreciated by those skilled in the art that the puncture could be made in other areas of the body in order to gain access to the desired body cavity and/or body organ. The catheter 24 is inserted into the open end which is generally along the axis of the sheath introducer. Both the sheath introducer 21 and the catheter 24 are thus within the patient's body, and the catheter is moved within the body vessel as desired. In the illustrated embodiment, this movement is to a location within the heart 27. More specifically, the catheter having its electrically conductive electrode is moved manually through the sheath, up through the patient's abdomen and thorax until it is in contact with the heart.

The pin jack 32 or other suitable connector at the end of the conductor 31 accesses the system to equipment needed for carrying out the desired medical procedure. For example, when mapping is to be accomplished, this piece of equipment (not shown) can be a recording apparatus for measuring the electrical potential of the heart. Alternatively, other equipment could be incorporated, such as energy generating equipment for carrying out ablation procedures and the like. It will be appreciated that thus two electrical contacts are provided within the body, one by the electrode(s) of the catheter 24, and the other the electrically conductive portions of the sheath introducer 21. The electrical circuit thus completed permits the electrical potential of the heart to be measured on the recorder. Alternatively, the electrical circuit thus completed through the conductor 31 would allow for energy delivery, such as ablation energy, to be transmitted to the heart.

More particular reference is now made to the embodiments of the sheath introducer 21 which are illustrated, particularly in FIG. 1 through FIG. 4. The elongated conductive cannula shaft 22 is a polymeric cylinder 41 which has been rendered electrically conductive by adding a metallic component to it. In the embodiment illustrated in the drawings, the metallic component takes the form of an extremely thin adherent film of metallic material so as to provide the polymeric cylinder 41 with a conductive surface. In the preferred illustrated embodiment, this conductive surface is an external conductive surface 42. Electrically conductive surface 42 transforms the polymeric cylinder 41 into an indifferent electrode which is required for carrying out the procedures discussed herein. Optionally, an internal conductive surface 43 could be included if needed to provide adequate surface area for a particular metallic material. Typically, an internal conductive surface is not required and has a possible disadvantage of reducing flexibility of the cylinder 41 and can be susceptible to scratching when the catheter passes through.

In addition, it is necessary to provide secure electrical communication between the electrically conductive polymeric cylinder 41 and the conductor 31. In the illustrated embodiment, such is achieved by incorporating a conductive assembly component such as the illustrated stainless steel band 44. With this arrangement, assembly can be as follows. The tip of the conductor 31 is soldered to the inside surface of the band 44. The band is then press fitted onto a collar 45 of the sheath assembly. This assembly is then processed by an ion process deposition such that the electrically conductive surface covers the band 44 and at least a portion of the collar 45 in the area designated as 42a. As a result, the thin adherent metallic material coating is provided over the entire cannula shaft, over the collar and over the stainless steel band in order to create an electrically conductive path from the distal tip of the sheath 46 to the stainless steel band 44, through the conductor 31 and to the pin jack or the like 32.

As an alternative assembly approach, one could first apply the adherent metallic material coating onto the cannula shaft. Thereafter, one would then press fit the stainless steel band 44 and the conductor end over the metallicized shaft and/or metallicized collar 45. In this instance as well, an electrically conductive path is provided from the distal tip 46 to the pin jack or the like 32.

A typical polymeric cylinder 41 of the cannula shaft will be made of a material that is somewhat flexible but yet has adequate rigidity to perform as a cannula sheath. Included are polyamide elastomers which are relatively high on the Durometer hardness scale for polyamide elastomers. Typically, such hardnesses would be on the order of 60D and above. Other catheter sheath materials which can be formulated to provide the desired flexibility and strength are polyurethanes, polyethylenes, nylons including polyamide homopolymers and polyamide copolymers, and Teflon compounds. An exemplary polyamide material that is used in current sheaths that are typically not of the electrically conductive type but which can be modified according to the present invention is PEBAX 70D polyamide, which is a polyester ether block copolymer of a nylon block with an ether block.

The conductive surface of extremely thin film of metallic material is preferably applied by ion process deposition of a metal element, metal alloy or metal compound onto the sheath. The conductive surface should remain malleable enough to withstand flexing of the shaft without flaking off from the shaft. It is important that the metallic material be spread over a large surface area inasmuch as an enhanced surface area decreases impedance. For example, it is advantageous that the metallic material surface area of the sheath be substantially greater than that of the electrode(s) 25 and/or 26 at the distal portion of the catheter 24. This difference in respective conductive surface areas substantially reduces or virtually eliminates the chance of surface heating of the indifferent electrode when the RF current is passed through the active electrode.

An example of a suitable ion process deposition of the metallic material is one available from Spire Corporation, of Bedford, Massachusetts. Some such processes are identified as SPI-ARGENT and SPI-MET (trademarks) procedures. Such are especially suitable for metallizing polymeric surfaces and can provide the desired thin film of metallic material that is characteristic of the present invention. The basic procedure is one of ion process deposition.

Generally speaking, processes suitable for the present invention can be characterized as achieving chemical vapor deposition. A rastered ion beam of a suitable chemical can also be applied such that the metallic material is "pounded" and bonded into the polymer by being bombarded by the ion beam. The result is a very thin, highly adherent metallic material film that is both mechanically and chemically bonded to the polymeric cylinder 41. Surface area enlargement or enhancement can also be achieved by further raster ion beam bombardment in order to "dimple" or texture the deposited metallic material surface. An example is the SPI-TEXT (trademark) process of Spire Corporation.

Patents which disclosure these procedures and related equipment and specific materials and processing conditions include U.S. Pat. Nos. 4,229,232, 4,443,488, 4,693,760, 4,743,493, 5,104,690, 5,118,400, 5,123,924, 5,133,757 and 5,236,509. These disclosures are incorporated by reference hereinto.

It will be appreciated that, if the film is too thick, it will rigidify the polymeric cylinder too severely, and it will lose the flexibility and feel normally associated with catheter sheath introducers. If the metallic material does not adhere adequately and merely encapsulates the polymeric surface, rather than being bonded to it and into it, delamination will be a problem. Also, a very thin material which is well bonded to and into the surface of the polymeric material will run substantially no risk of interfering with or "catching" around the puncture 38 or elsewhere when structures such as ring electrodes or strip electrodes are avoided. The metallic material coating does not significantly negatively modify the mechanical properties of the sheath cannula and in fact can enhance mechanical tear and puncture resistance properties.

A suitable very thin, highly adherent metallic material coating will be not greater than about 10 microns in thickness, preferably not greater than about 5 microns. A suitable exemplary thickness is about 1 to 4 microns. Either a single metal, metal alloy or metal compound deposition or a multiple metallic material deposition can be carried out. For example, some metallic materials have especially high conductivity or low resistivity while others, although having suitable electrical properties, are particularly well suited because of especially high biocompatibility or inertness within an in vivo setting, making them especially advantageous as an external coating.

It has been found that the conducting metallic material should have a resistivity of equal to or less than about 50 microhm-centimeters at 20° C. or that the entire sheath introducer should have a resistance of less than about 3 ohms at a coating thickness of about 10 microns or less. The metallic materials should also be biocompatible.

Examples of materials that meet these resistivity and biocompatibility criteria include gold, Monel metal alloy, platinum, silver, steel alloys such as stainless steel, tantalum, titanium and titanium nitride. Generally, metallic materials suitable for use as pacemaker electrodes should meet the criteria for the metallic material of the present invention.

The following is a listing of metallic elements or metallic alloys that exhibit the desired resistivity and theoretical resistance discussed herein. These data are theoretical resistance calculations for selected conductors. The cannula segment length used was 10.8 cm. and the size used was 8F, its outer diameter being 0.2667 cm. These resistivity and resistance calculations are as follows:

| Metallic Material | Coating and Thickness | Resistivity at 20° C. (Microhms-cm) | Cannula Theoretical Resistance at 37° C. (ohms) |
| --- | --- | --- | --- |
| gold | 3 | 2.44 | 1.37 |
| gold | 4 | 2.44 | 0.10 |
| Monel metal | 3 | 42 | 19.38 |
| Monel metal | 4 | 42 | 1.45 |
| platinum | 3 | 10.6 | 5.22 |
| platinum | 4 | 10.6 | 0.39 |
| silver | 3 | 1.59 | 0.84 |
| silver | 4 | 1.59 | 0.06 |
| steel (E.B.B) | 3 | 10.4 | 5.29 |
| steel (E.B.B) | 4 | 10.4 | 0.40 |
| tantalum | 3 | 15.5 | 7.42 |
| tantalum | 4 | 15.5 | 0.56 |
| titanium | 3 | 42 | 18.05 |
| titanium | 4 | 42 | 1.35 |

In an exemplary procedure, silver metal was deposited by the Spire process to 3000 angstroms in thickness. Resistance was measured to be in the range of about 1 ohm, which generally corresponds to these data. For example, titanium deposited to a thickness of about 4 microns should show the resistance of the shaft to be on the order of 1.35 ohm. In other examples, titanium was deposited to a thickness of 500 angstroms, and titanium nitride was also suitably deposited. Desirably, the resistance of the sheath introducer at body temperature, 37° C., should be on the order of about 1 ohm or less. This resistance should occur for coating thicknesses of less than 10 microns, including those as thin as 3 or 4 microns, or less, as illustrated by the above data. Measured DC resistance should be 10 ohms or less, at 37° C.

In an especially preferred arrangement, a PEBAX 70D polymeric cylinder is subjected to ion process deposition of silver. This provides a base coating which is extremely electrically conductive. This is followed by ion process deposition of gold metal thereonto in order to enhance the inertness of the metallic material deposition to the body. The total metallic material thus coated had a thickness of approximately 2 microns. The resulting cannula sheath introducer was found to function as an indifferent electrode having an extremely low resistance and a feel and appearance which is difficult to discern from the same introducer that does not exhibit the electrical properties of the present invention. Typical sheath cannula sizes in this regard are on the order of 6 French, 7 French and 8 French.

It will be understood that the embodiments of the present invention which have been described are illustrative some of the applications of the principles of the present invention. Numerous modifications may be made by those skilled in the art without departing from the true spirit and scope of the invention.

We claim:

1. An electrically conductive percutaneous unipolar vascular sheath introducer, comprising:

an elongated conductive cannula shaft having a generally cylindrical shaft component made of polymeric material, said elongated conductive cannula shaft having a proximal end portion, a distal end portion, an elongated generally cylindrical outer surface and an elongated generally cylindrical inner surface defining an elongated bore for receiving a catheter;

a hub secured to said proximal portion of the elongated conductive cannula shaft;

said elongated generally cylindrical outer surface is an electrically conductive surface which is an adherent thin metallic material film;

a conductor lead electrically connected to said elongated electrically conductive generally cylindrical outer surface, said elongated conductive cannula shaft being an indifferent electrode having a surface area substantially coincident with at least said elongated generally cylindrical outer surface; and said metallic material film is a multilayered film having an internal silver layer of exceedingly low resistivity and an outer gold layer of low resistivity and exceedingly high inertness, the resistivity of the internal layer being less than the resistivity of the outer layer, and the inertness of the outer layer being greater than that of the internal layer.

2. The electrically conductive sheath introducer in accordance with claim 1, wherein said metallic surface is of a metallic material having a resistivity of not greater than about 50 microhm-centimeters at 20° C.

3. The electrically conductive sheath introducer in accordance with claim 1, wherein said metallic surface has a thickness of not greater than about 10 microns and has a resistance of not greater than about 3 ohms.

4. The electrically conductive sheath introducer in accordance with claim 1, wherein said conductor lead is electrically connected to said outer surface with a band that is electrically conductive.

5. The electrically conductive sheath introducer in accordance with claim 4, wherein said adherent thin metallic material film is substantially continuous along said generally cylindrical outer surface and said band.

6. The electrically conductive sheath introducer in accordance with claim 4, wherein said metallic material film extends from said distal end portion of the shaft component to said band.

7. The electrically conductive sheath introducer in accordance with claim 1, wherein said metallic material film extends from said distal end portion of the shaft component to the location at which said conductor lead is electrically connected to said shaft component.

8. The electrically conductive sheath introducer in accordance with claim 1, wherein said metallic surface has a thickness of not greater than about 5 microns.

9. The electrically conductive sheath introducer in accordance with claim 1, wherein said indifferent electrode of the sheath introducer has a resistance of not greater than approximately 2 ohms.

10. The electrically conductive sheath introducer in accordance with claim 1, wherein said indifferent electrode of the sheath introducer has a resistance of not greater than approximately 1 ohm.

11. The electrically conductive sheath introducer in accordance with claim 1, wherein said metallic material film is selected from the group consisting of gold, platinum, silver, tantalum and titanium materials.

12. An electrically conductive percutaneous unipolar vascular sheath introducer, comprising:

an elongated conductive cannula shaft having a generally cylindrical shaft component made of polymeric material, said elongated conductive cannula shaft having a proximal end portion, a distal end portion, an elongated generally cylindrical outer surface and an elongated generally cylindrical inner surface defining an elongated bore for receiving a catheter;

a hub secured to said proximal portion of the elongated conductive cannula shaft;

said elongated generally cylindrical outer surface is an electrically conductive surface which is an adherent thin metallic material film;

a conductor lead electrically connected to said elongated electrically conductive generally cylindrical outer surface, said elongated conductive cannula shaft being an indifferent electrode having a surface area substantially coincident with at least said elongated generally cylindrical outer surface; and said elongated generally cylindrical inner surface is an electrically conductive surface which is an adherent thin metallic material film, and said electrically conductive inner surface is included in said indifferent electrode, said indifferent electrode having a surface area substantially coincident with both said elongated outer surface and said elongated inner surface.

13. The electrically conductive sheath introducer in accordance with claim 12, wherein said metallic outer surface is of a metallic material having a resistivity of not greater than about 50 microhm-centimeters at 20° C.

14. The electrically conductive sheath introducer in accordance with claim 12, wherein said metallic outer surface has a thickness of not greater than about 10 microns and has a resistance of not greater than about 3 ohms.

15. The electrically conductive sheath introducer in accordance with claim 12, wherein said conductor lead is electrically connected to said outer surface with a band that is electrically conductive.

16. The electrically conductive sheath introducer in accordance with claim 15, wherein said outer surface adherent thin metallic material film is substantially continuous along said generally cylindrical outer surface and said band.

17. The electrically conductive sheath introducer in accordance with claim 15, wherein said outer surface metallic material film extends from said distal end portion of the shaft component to said band.

18. The electrically conductive sheath introducer in accordance with claim 12, wherein said outer surface metallic material film extends from said distal end portion of the shaft component to the location at which said conductor lead is electrically connected to said shaft component.

19. The electrically conductive sheath introducer in accordance with claim 12, wherein said metallic outer surface has a thickness of not greater than about 5 microns.

20. The electrically conductive sheath introducer in accordance with claim 12, wherein said indifferent electrode of the sheath introducer has a resistance of not greater than approximately 2 ohms.

21. The electrically conductive sheath introducer in accordance with claim 12, wherein said indifferent electrode of the sheath introducer has a resistance of not greater than approximately 1 ohm.

22. The electrically conductive sheath introducer in accordance with claim 12, wherein said outer surface metallic material film is selected from the group consisting of gold, platinum, silver, tantalum and titanium.

23. The electrically conductive sheath introducer in accordance with claim 12, wherein said outer surface metallic material film is a multilayered film having an internal layer of exceedingly low resistivity and an outer layer of low resistivity and exceedingly high inertness, the resistivity of the internal layer being greater than the resistivity of the outer layer, and the inertness of the outer layer being greater than that of the internal layer.

24. The electrically conductive sheath introducer in accordance with claim 23, wherein said internal layer is silver and said outer layer is gold.

25. A catheter and sheath introducer assembly, comprising:
 a catheter having an elongated flexible shaft, a hub at a proximal portion thereof, and an electrode at a distal portion thereof;
 an electrically conductive percutaneous vascular sheath introducer including:
  an elongated conductive cannula shaft having a generally cylindrical shaft component made of polymeric material, said elongated conductive cannula shaft having a proximal end portion, a distal end portion, an elongated generally cylindrical outer surface and an elongated generally cylindrical inner surface defining an elongated bore for receiving said catheter,
  a hub secured to said proximal portion of the elongated conductive cannula shaft,
  said elongated generally cylindrical outer surface is an electrically conductive surface which is an adherent thin metallic material film,
  a conductor lead electrically connected to said elongated electrically conductive generally cylindrical outer surface, said elongated conductive cannula shaft being an indifferent electrode having a surface area substantially coincident with at least said elongated generally cylindrical outer surface;
  said conductor lead is adapted to be electrically connected to a circuit external of a patient's body, and said indifferent electrode is adapted to be a component of an electrical circuit passing through patient's body between the electrode of the catheter and the elongated conductive cannula shaft, wherein the metallic surface is a textured metallic surface which is mechanically bonded and chemically bonded by chemical vapor deposition ion beam bombardment to said elongated generally cylindrical outer surface of the shaft component made of polymeric material; and
  said elongated generally cylindrical inner surface includes an electrically conductive surface which is an adherent thin metallic material film, and said inner electrically conductive surface is included in said indifferent electrode.

26. The assembly in accordance with claim 25, wherein said metallic surface is of a metallic material having a resistivity of not greater than about 50 microhm-centimeters at 20° C.

27. The assembly in accordance with claim 25, wherein said metallic surface has a thickness of not greater than about 10 microns and has a resistance of not greater than about 3 ohms.

28. The assembly in accordance with claim 25, wherein said metallic material film extends from said distal end portion of the shaft component to the location at which said conductor lead is electrically connected to said shaft location.

29. The assembly in accordance with claim 25, wherein said electrode of the catheter has a surface area which is substantially less than that of said indifferent electrode of the sheath introducer.

* * * * *

UNITED STATES PATENT AND TRADEMARK OFFICE
CERTIFICATE OF CORRECTION

PATENT NO.  : 5,733,323
DATED       : March 31, 1998
INVENTOR(S) : Jerrick Buck, Daniel S. Goldman and Donald J. Larnard It is certified that error appears in the above-indentified patent and that said Letters Patent is hereby corrected as shown below:

On the title page,

Item [56] "References Cited", Patent No. 4,743,493 "Siochansi et al" should read --Sioshansi et al--; for the "Attorney, Agent, or Firm", delete "Fitz-Gibbon" and insert --FitzGibbon--.
Col. 1, line 32, delete "Such" and insert --such--.
Col. 6, line 63, "illustrative some" should read --illustrative of some--.
Col. 8, line 2, delete "materials".
Col. 10, line 6, "through patient's" should read --through the patient's--.

Signed and Sealed this

Eleventh Day of May, 1999

Attest:

Q. TODD DICKINSON

*Attesting Officer*  *Acting Commissioner of Patents and Trademarks*